US009295722B2

(12) United States Patent
Savage et al.

(10) Patent No.: US 9,295,722 B2
(45) Date of Patent: Mar. 29, 2016

(54) BACTERIAL GLYCOLIPID ACTIVATION OF CD1D-RESTRICTED NKT CELLS

(75) Inventors: Paul B. Savage, Mapleton, UT (US); Albert Bendelac, Chicago, IL (US); Luc Teyton, Del Mar, CA (US)

(73) Assignees: THE SCRIPPS RESEARCH INSTITUTE, La Jolla, CA (US); THE UNIVERSITY OF CHICAGO, Chicago, IL (US); BRIGHAM YOUNG UNIVERSITY, Provo, UT (US)

( * ) Notice: Subject to any disclaimer, the term of this patent is extended or adjusted under 35 U.S.C. 154(b) by 1443 days.

(21) Appl. No.: 11/814,103

(22) PCT Filed: Jan. 26, 2006

(86) PCT No.: PCT/US2006/002781
§ 371 (c)(1),
(2), (4) Date: Apr. 11, 2008

(87) PCT Pub. No.: WO2006/083671
PCT Pub. Date: Aug. 10, 2006

(65) Prior Publication Data
US 2008/0279894 A1    Nov. 13, 2008

Related U.S. Application Data

(60) Provisional application No. 60/648,153, filed on Jan. 28, 2005.

(51) Int. Cl.
| | |
|---|---|
| A61K 39/00 | (2006.01) |
| C07H 17/02 | (2006.01) |
| A61K 31/70 | (2006.01) |
| A61K 31/74 | (2006.01) |
| A61K 39/39 | (2006.01) |
| A61K 31/7032 | (2006.01) |
| A61K 35/74 | (2015.01) |
| A61K 38/17 | (2006.01) |

(52) U.S. Cl.
CPC ............ *A61K 39/39* (2013.01); *A61K 31/7032* (2013.01); *A61K 35/74* (2013.01); *A61K 38/1774* (2013.01); *A61K 2039/55594* (2013.01)

(58) Field of Classification Search
None
See application file for complete search history.

(56) References Cited

U.S. PATENT DOCUMENTS

| | | | |
|---|---|---|---|
| 5,604,207 A | 2/1997 | DeFrees et al. | |
| 5,767,092 A | 6/1998 | Koezuka et al. | |
| 5,780,441 A | 7/1998 | Higa et al. | |
| 5,849,716 A | 12/1998 | Akimoto et al. | |
| 5,936,076 A | 8/1999 | Higa et al. | |
| 6,071,884 A | 6/2000 | Koezuka et al. | |
| 6,531,453 B1 | 3/2003 | Taniguchi et al. | |
| 6,747,010 B2 | 6/2004 | Taniguchi et al. | |
| 7,273,852 B2 | 9/2007 | Tsuji et al. | |
| 2002/0071842 A1* | 6/2002 | Gumperz et al. | 424/143.1 |
| 2002/0115624 A1* | 8/2002 | Behar et al. | 514/42 |
| 2003/0139351 A1 | 7/2003 | Taniguchi et al. | |
| 2003/0153514 A1 | 8/2003 | Yagita | |
| 2003/0157135 A1 | 8/2003 | Tsuji et al. | |
| 2003/0206914 A1* | 11/2003 | Porcelli et al. | 424/184.1 |
| 2004/0127429 A1* | 7/2004 | Tsuji | 514/23 |
| 2004/0266726 A1 | 12/2004 | Yagita | |
| 2006/0073118 A1 | 4/2006 | Bendelac et al. | |
| 2006/0264382 A1 | 11/2006 | Savage et al. | |
| 2008/0095787 A1 | 4/2008 | Teyton et al. | |

FOREIGN PATENT DOCUMENTS

| | | |
|---|---|---|
| WO | 2003/018039 | 3/2003 |
| WO | WO 2004/094444 | 11/2004 |
| WO | WO 2005/000348 | 1/2005 |
| WO | WO 2007/118234 | 10/2007 |
| WO | WO 2008/005824 | 1/2008 |

OTHER PUBLICATIONS

Savage et al (Organic Letters, 2002, 4(8), 1267-70).*
Kawano et al (Science, 1997, 278, 1626-29).*
Kosako et al. 2000 (Proposal of Sphingomonadaceae Fam. Nov., consisting of ... with the Type Genus *Sphingomonas* Yabuuchi et al. 1990) in Microbiol. Immunol. 44(7): 563-575.*
Wu et al. Jan. 21, 2005; Bacterial glycolipids and analogs as antigens for CD1d-restricted NKT cells, PNAS 102(5):1351-1356.*
Hansen et al. 2004; Regulation of immunity and pathogenesis in infectious diseases by CD1d-restricted NKT cells, Internation Journal for Parasitology 34:15-25.*
Kosako et al. 2000 (Microbiol. Immunol. 44(7) 563-575).*
Hansen et al. 2004 (Regulation of Immunity and pathogenesis in infectious disease by CD1d-restricted NKT cells, International Journal for Parasitology 34:15-25).*
Deng et al. 2011 (Impact of sugar stereochemistry on natural killer T cell stimulation by bacterial glycolipids; Org. Biomol. Chem. 9(22):7659-7662).*
Brigl, M. et al., "CD1: T cell function and antigen presentation," Annu. Rev. Immunol. (2004) 22:817-890.
Corey et al., "A new method for the synthesis of organic nitro compounds," J. Am. Chem. Soc. (1984) 106:3682-3683.
Dascher, C.C. et al., "CD1 Antigen Presentation and Infectious Disease," Contributions to Microbiology (2003) 10:164-182.
Davis, N.J. et al., "Chemical Synthesis of Disaccharides Which are Partial Structures of the Glycosaminoglycan Heparan Sulfate," J. Chem. Soc. (1994) 1:359-368.
Gui, M. et al., "TCR beta chain influences but does not solely control autoreactivity of V alpha 14J28IT cells," J. Immunol. (2001) 167(11):6239-6246.

(Continued)

*Primary Examiner* — Gary Nickol
*Assistant Examiner* — Mary Lyons
(74) *Attorney, Agent, or Firm* — Merchant & Gould P.C.

(57) ABSTRACT

Disclosed are methods for activating an NKT cell, methods of stimulating an immune response in a subject, methods of improving vaccine efficacy, and methods of treating an infection. Also disclosed are methods of promoting tumor rejection, treating cancer, modulating autoimmunity and inhibiting allergen-induced hypersensitivity in subjects. The methods include contacting an NKT cell with a bacterial glycolipid complexed with a CD1 molecule to activate the NKT cell. The bacterial glycolipid may be derived from a member of the Class Alphaproteobacteria.

10 Claims, 7 Drawing Sheets

(56) References Cited

OTHER PUBLICATIONS

Gumperz, J.E. et al., "Functional distinct subsets of CD1d-restricted natural killer T cells revealed by CD1d tetramer staining," J. Exp. Med. (2002) 195(5):625-636.

Hashimoto, S. et al., "Glycosylation Using Glucopyranosyl Fluorides and Silicon-Based Catalysts, Solvent Dependency of the Stereoselection," Tetrahedron Letters (1984) 25:13:1379-1382.

Hayashi, M. et al., "Simple Synthesis of Glycosyl Fluorides," Chem. Letters (1984) 1747-1750.

Karadimitris, A. et al., "Human CD1d-glycolipid tetramers generated by in vitro oxidative refolding chromatography," Proc. Natl. Acad. Sci. USA (2001) 98(6):3294-3298.

Kawano, T. et al., "CD1d-restricted and TCR-mediated activation of Vα14 NKT cells by glycosylceramides," Science (1997) 278:1626-1629.

Khan, M. et al., "Syntheses and Antiinflammatory Activity of Some 6-aryl-2,3,4,5-tetrahydro-3-pyridazinones," Indian J. Chem. (2000) 39B:614-619.

Kronenberg, M., "Toward an understanding of NKT cell biology: progress and paradoxes," Ann. Rev. Immunol (2005) 23:877-900.

Lee, P.T. et al., "Testing the NKT cell hypothesis on human IDDM pathogenesis," J. Clin. Invest. (2002) 110(6):793-800.

Lei, P.-S. et al., "Synthesis of a 3-deoxy-L-iduronic acid containing heparin pentasaccharide to probe the conformation of the antithrombin III binding sequence," Bioorg. Med. Chem. (1998) 6:1337-1346.

Matsuda, J.L. et al., "Tracking the response of natural killer T cells to a glycolipid antigen using CD1d tetramers," J. Exp. Med. (2000) 192(5):741-753.

Miyamoto, K. et al., "A Synthetic Glycolipid Prevents Autoimmune Encephalomyelitis by Inducing TH2 Bias of Natural Killer T Cells," Nature (2001) 413:531-534.

Morita, M. et al., "Structure-Activity Relationship of α-Galactosylceramides Against B16-Bearing Mice," J. Med. Chem. (1995) 38:2176-2187.

Nakagawa, R. et al., "Mechanisms of the Antimetastatic Effect in the Liver and of the Hepatocyte Injury Induced by α-Galactosylceramide in Mice," J. Immun. (2001) 166:11:6578-6584.

Pal, E. et al., "Costimulation-Dependent Modulation of Experimental Autoimmune Encephalomyelitis by Ligand Stimulation of Vα14 NK T Cells," J. Immunol. (2001) 166:662-668.

Park, S.H. et al., "CD1-restricted T-cell responses and microbial infection," Nature (2000) 406:788-792.

Park, S.H. et al., "The Mouse CD1d-restricted Repetoire is Dominated by a Few Autoreactive T cell Receptor Families," J. Exp. Med. (2001) 8:893-904.

Sakai, T. et al., "Effects of α- and β-Galactosylated C2-Ceramides on the Immune System," J. Med. Chem. (1998) 41:650-652.

Sidobre, S. et al., "CD1d tetramers: a powerful tool for the analysis of glycolipid reactive T cells," J. Immunol. Methods (2002) 268:107-121.

Singh, P.P. et al., "The Synthesis of 2,3,4,6,7-Penta-O-Methyl-D-glycero-L-manno-Heptose and 2,4,6,7-Tetra-O-Methyl-D-glycero-L-manno-Heptose," Carbohydrate Res. (1970) 12:261-266.

Takikawa et al., "Diastereoselective Epoxidation of the Double Bond at C-4 of Sphingosines to Provide Phytosphingosine Relatives such as α-Galactosylceramide KRN7000," Tetrahedron (1998) 54:3141-3150.

Van Kaer, L., "Alpha-galactosylceramide therapy for autoimmune diseases: prospects and obstacles," Nat. Rev. Immunol. (2005) 5:31-42.

Vaultier, M. et al., Tetrahedron Letters (1983) 24:763.

Wang, B. et al., "CD1-Restricted NK T Cells Protect Nonobese Diabetic Mice from Developing Diabetes," J. Exp. Med. (2001) 194:313-319.

Wang, F. et al., "Tuning of Binding Selectivity: Metal Control of Organic Guest Binding and Allosteric Perturbation of Fluorescent Metal Sensor," J. Org. Chem. (1999) 64:8922-8928.

Weber, G. et al., "Synthesis and Spectral Properties of a Hydrophobic Fluorescent Probe: 6-Propionyl-2-(dimethylamino) naphthalene," Biochem. (1979) 18:14:3075-3078.

Zhou et al., "Synthesis and NKT cell stimulating properties of fluorophore-and biotin-appended 6"-amino-6"-deoxy-galactosylceramides," Org. Lett. (2002) 4(8):1267-1270.

International Search Report and Written Opinion of International Searching Authority of PCT/US2007/072451 dated Nov. 27, 2007.

International Search Report and Written Opinion of International Searching Authority of PCT/US06/002781 dated Dec. 20, 2006.

Supplementary Search Report of the European Patent Office for Application No. 03816701.1 dated Sep. 17, 2007.

European Office Action for Application No. 03816701.1 dated Nov. 29, 2007.

United States Patent Office action for U.S. Appl. No. 10/550,165 dated Jan. 9, 2008.

United States Patent Office action for U.S. Appl. No. 10/550,165 dated Jul. 20, 2007.

Written Opinion of International Preliminary Examining Authority for International Application No. PCT/US03/08530 dated Jun. 30, 2005.

International Search Report of International Searching Authority for Application No. PCT/US03/08530 dated Aug. 3, 2004.

International Search Report and Written Opinion of International Searching Authority for International Application No. PCT/US07/66250 dated Oct. 15, 2007.

Goodman & Gilman's The Pharmacological Basis of Therapeutics, Tenth Edition, Hardman and Limbird, editors, The McGraw-Hill Companies, Inc., New York (2001) 54-56.

Gupta, R.K. et al., "Adjuvants—a balance between toxicity and adjuvanticity," Vaccine (1993) 11(3):293-306.

Deng et al., "Impact of Sugar Stereochemistry on Natural Killer T Cell Stimulation by Bacterial Glycolipids", Org. Biomol. Chem., Oct. 26, 2011; 9 (22): 7659-7662, 10 pages.

Ando, H. et al., "Solid-phase capture-release strategy applied to oligosaccharide synthesis on a soluble polymer support," Angew. Chem. Int. Ed. (2001) 40:4725-4728.

Bendelac, A. et al., "Increased interleukin 4 and immunoglobulin E production in transgenic mice overexpressing NK1 T cells," J. Exp. Med. (1996) 184:1285-1293.

Benlagha, K. et al., "In vivo identification of glycolipid antigen-specific T cells using fluorescent CD1d tetramers," J. Exp. Med. (2000) 191:1895-1903.

Brigl, M. et al., "Mechanism of CD1d-restricted natural killer T cell activation during microbial infection," Nat. Immunol. (2003) 4:1230-1237.

Cantu, C. et al., "The paradox of immune molecular recognition of alpha-galactosylceramide: low affinity, low specificity for CD1d, high affinity for alpha beta TCRs," J. Immunol (2003) 170:4673-4682.

Fujii, S-I. et al., "Activation of natural killer T cells by alpha-galactosylceramide rapidly induces the full maturation of dendritic cells in vivo and thereby acts as an adjuvant for combined CD4 and CD8 T cell immunity to a coadministered protein," J. Exp. Med. (2003) 198:267-279.

Garrity, G.M. et al., Taxonomic Outline of the Procaryotic Genera, Bergey's Manual of Systematic Bacteriology, 2nd Edition (Apr. 2001).

Godfrey, D.I. et al., "Going both ways: immune regulation via CD1d-dependent NKT cells," J. Clin. Invest. (2004) 114(10):1379-1388.

Godfrey, D.I. et al., "The elusive NKT cell antigen—is the search over?" Science (2004) 306:1687-1688.

Iida, N. et al., "A sulfated glucosylceramide from rat kidney," J. Biol. Chem. (1989) 264:5974-5980.

Ismail, N. et al., "Overproduction of TNF-alpha b CD8+ type 1 cells and down-regulation of IFN-γ production by CD4+ Th1 cells contribute to toxic shock-like syndrome in an animal model of fatal monocytotropic ehrlichiosis," J. Immunol. (2004) 172:1786-1800.

Kinjo, Y. et al., "Recognition of bacterial glycosphingolipids by natural killer T cells," Nature (2005) 434:520-525.

(56) References Cited

OTHER PUBLICATIONS

Mattner, J. et al., "Exogenous and endogenous glycolipid antigens activate NKT cells during microbial infections," Nature (2005) 434:525-529.

Petrovsky, N. et al., "Vaccine adjuvants: current state and future trends," Immunol. Cell Biol. (2004) 82:488-496.

Rock, K.L. et al., "Natural endogenous adjuvants," Springer Semin. Immunopathol. (2005) 26:231-246.

Wu et al., "Bacterial glycolipids and analogs as antigen for CD1d-restricted NKT cells," PNAS (2005) 102(5):1351-1356.

Zajonc, D.M. et al., "Structure and function of a potent agonist for the semi-invariant natural killer T cell receptor," Nat. Immunol (2005) 6:810-818.

Zhou, D. et al., "Lysosomal glycosphingolipid recognition by NKT cells," Science (2004) 306:1786-1789.

Brutkiewicz, R.R. et al., "CD1d-mediated antigen presentation to natural killer T (NKT) cells," Critical Reviews in Immunology (2003) 23:403-419.

Brutkiewicz, R.R. et al., "Natural killer T (NKT) cells and their role in antitumor immunity," Critical Reviews in Oncology/Hematology (2002) 41:287-298.

Liu, Y. et al., "A modified alpha-galactosyl ceramide for staining and stimulating natural killer T cells," J. Immun. Meth. (2006) 312(1-2):34-39.

Singh, A.K. et al., "The natural killer T cell ligand alpha-galactosylceramide protects mice against EAE by an IL-4- and IL-10-dependent mechanism," FASEB J. Fed. of Amer. Soc. for Exp. Bio. (2002) 16:A1043.

Yu, K.O.A. et al., "Modulation of CD1d-restricted NKT cell responses by using N-acyl variants of alpha-galactosylceramides," Proc. Natl. Acad. Sci. USA (2005) 102(9):3383-3388.

* cited by examiner

BACTERIAL GLYCOLIPID ACTIVATION OF CD1D-RESTRICTED NKT CELLS

CROSS-REFERENCE TO RELATED APPLICATIONS

This application is a national stage filing under 35 U.S.C. 371 of International Application No. PCT/US2006/002781 filed on Jan. 26, 2006, which claims the benefit of U.S. provisional application 60/648,153 filed on Jan. 28, 2005. These applications are incorporated herein by reference.

STATEMENT REGARDING FEDERALLY SPONSORED RESEARCH

This invention was made with United States Government support awarded by the National Institutes of Health, National Institute of Allergy and Infectious Disease. A portion of the work described herein was supported by grant numbers AI 53725, GM 37969, AI 54523, QI 53725, DK 55037, AI 42267, and DK 6172 from the National Institutes of Health. The United States Government has certain rights in this invention.

INTRODUCTION

The CD1d molecule is a member of the CD1 family of β2 microglobulin-associated molecules. In contrast to class I and II major histocompatibility complex (MHC) molecules that present protein antigens to CD8+ and CD4+ T cells, respectively, CD1 molecules have evolved to capture and process both foreign and self lipid antigens for display to T cells. CD1a, -b, and -c molecules have been shown to present foreign microbial antigens to human TCRαβ T cells. In contrast, CD1d-restricted T cells, or NKT cells, are a population of innate-like memory/effector cells expressing both NK receptors and a conserved, semi-invariant TCR (Vα14-Jα18/Vβ8 in mice and Vα24-Jα18/Vβ11 in humans). Like NK cells, NKT cells constitutively express mRNA but not protein for IFN-γ, evidencing their poised effector stage. NKT cells have been implicated in suppression of autoimmunity and graft rejection, promotion of resistance to pathogens, and promotion of tumor immunity.

While NKT cells are known to respond to α-Galactosyl-Ceramide (αGal-Cer), a surrogate ligand derived from a marine sponge, lack of knowledge of their natural antigens has previously precluded understanding of the mechanisms of their peripheral activation and recruitment, as well as their thymic development.

The inventors have previously identified a natural endogenous antigen, isoglobotrihexosylceramide (iGb3), which is presented to NKT cells by LPS-activated dendritic cells. This work suggests that iGb3 is a primary ligand for NKT cells. However, the partial diversity of the β-chain of the TCR suggests that multiple natural antigen specificity may be possible.

SUMMARY

Described herein is the inventors' surprising discovery that glycolipids derived from members of the Class Alphaproteobacteria also act as natural ligands of CD1d molecules to activate NKT cells.

In one aspect, the invention provides a method of activating an NKT cell comprising contacting the NKT cell with a bacterial glycolipid complexed with a CD1d molecule. In some embodiments, the bacterial glycolipid may be derived from a member of the class Alphaproteobacteria.

In another aspect, the invention provides a method of inducing cytokine expression by an NKT cell comprising contacting a T-cell receptor of the NKT cell with a bacterial glycolipid complexed with a CD1d molecule.

In yet another aspect, the invention provides a method of stimulating an immune response in a subject comprising administering to the subject an effective amount of NKT cells activated by contacting a T-cell receptor of the NKT cells with a bacterial glycolipid complexed with a CD1d molecule.

In further aspects, the invention provides methods of improving vaccine efficacy, promoting tumor rejection, modulating autoimmunity, inhibiting allergen-induced hypersensitivity, and treating an infection in a subject by administration of an effective amount of a bacterial glycolipid derived from a member of the Class Alphaproteobacteria.

BRIEF DESCRIPTION OF THE DRAWINGS

FIG. 4A depicts in vivo activation of NKT cells 24 hours after intravenous infection with *Sphingomonas* ($1 \times 10^7$), *Ehrlichia* ($1 \times 10^8$) and *Salmonella* ($1 \times 10^6$). Similar results were obtained in 2 experiments.

FIG. 4B depicts IFN-γ production by NKT cells in response to *Salmonella*. The difference between $Hexb^{+/+}$ and $Hexb^{-/-}$ was significant for *Salmonella* (p=0.001). Three mice per group were analyzed and similar results obtained in 2 independent experiments.

FIG. 4C depicts bacterial burden in the lungs of $CD1d^{+/-}$ and $CD1d^{-/-}$ mice after infection with the indicated CFU of

*Sphingomonas* (each bar represents 4 to 5 mice). Fold increase and p values are indicated. Two representative experiments are shown.

Figure 4:
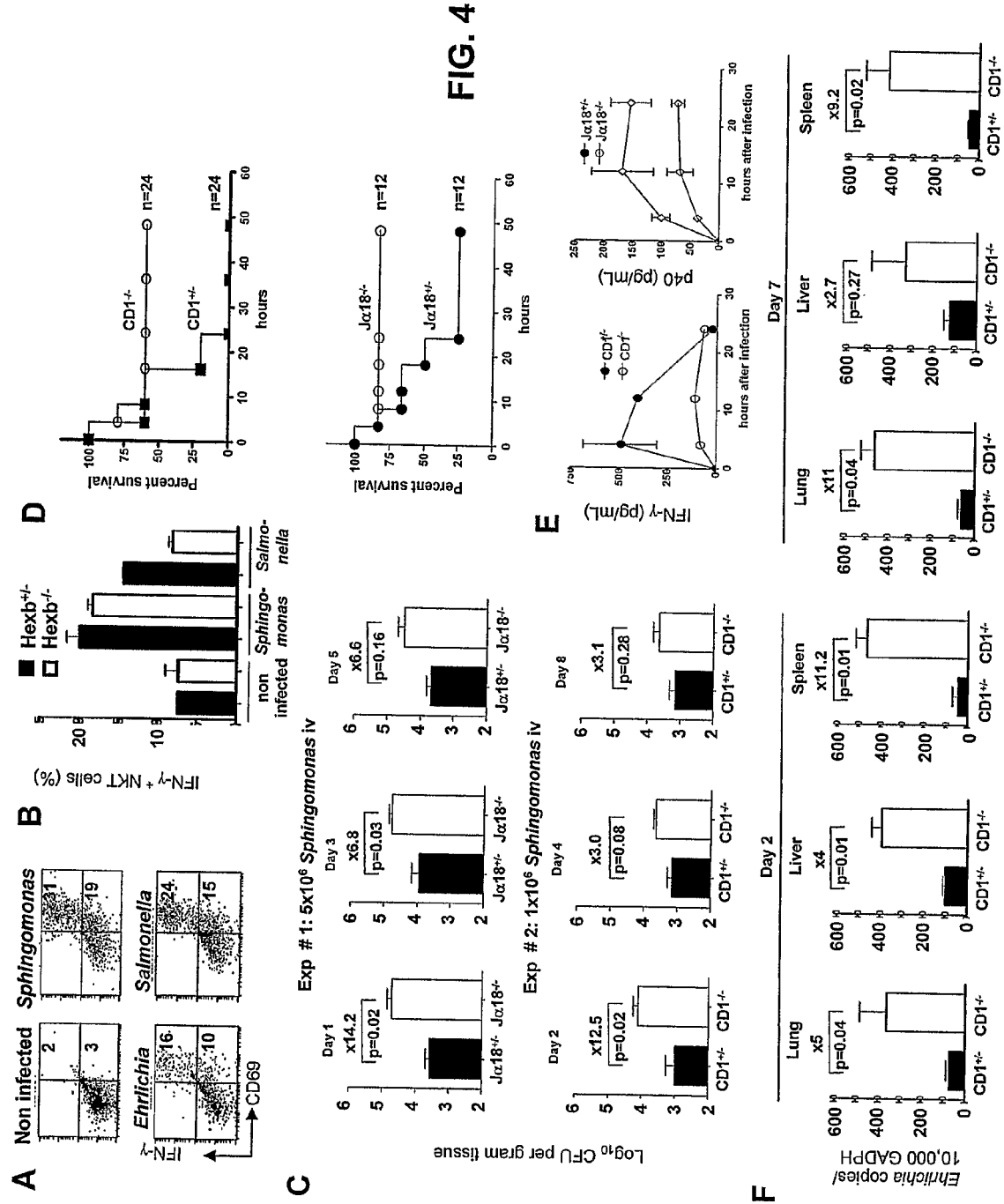

FIG. 4D depicts acute lethality in mice after inoculation of a high dose of $5 \times 10^8$ *Sphingomonas capsulata*. Separate experiments comparing $CD1d^{+/-}$ and $CD1d^{-/-}$ (n=24 each, p<0.0001) and $J\alpha18^{+/-}$ and $J\alpha18^{-/-}$ (n=12 each, p=0.034) are shown.

FIG. 4E depicts acute serum release of IFN-γ and IL-12 p40 in heterozygous and homozygous CD1d and Jα18 mutant mice and littermate controls after infection with $1 \times 10^7$ *Sphingomonas capsulata*. Similar results were obtained in 2 independent experiments.

FIG. 4F depicts *Ehrlichia* PCR counts in lungs, livers and spleens of $CD1d^{+/-}$ and $CD1d^{-/-}$ mice recovered at day 2 and day 7 post-infection (each bar represents 3 mice). Fold increase and p values are indicated. One representative experiment is shown.

Figure 5:
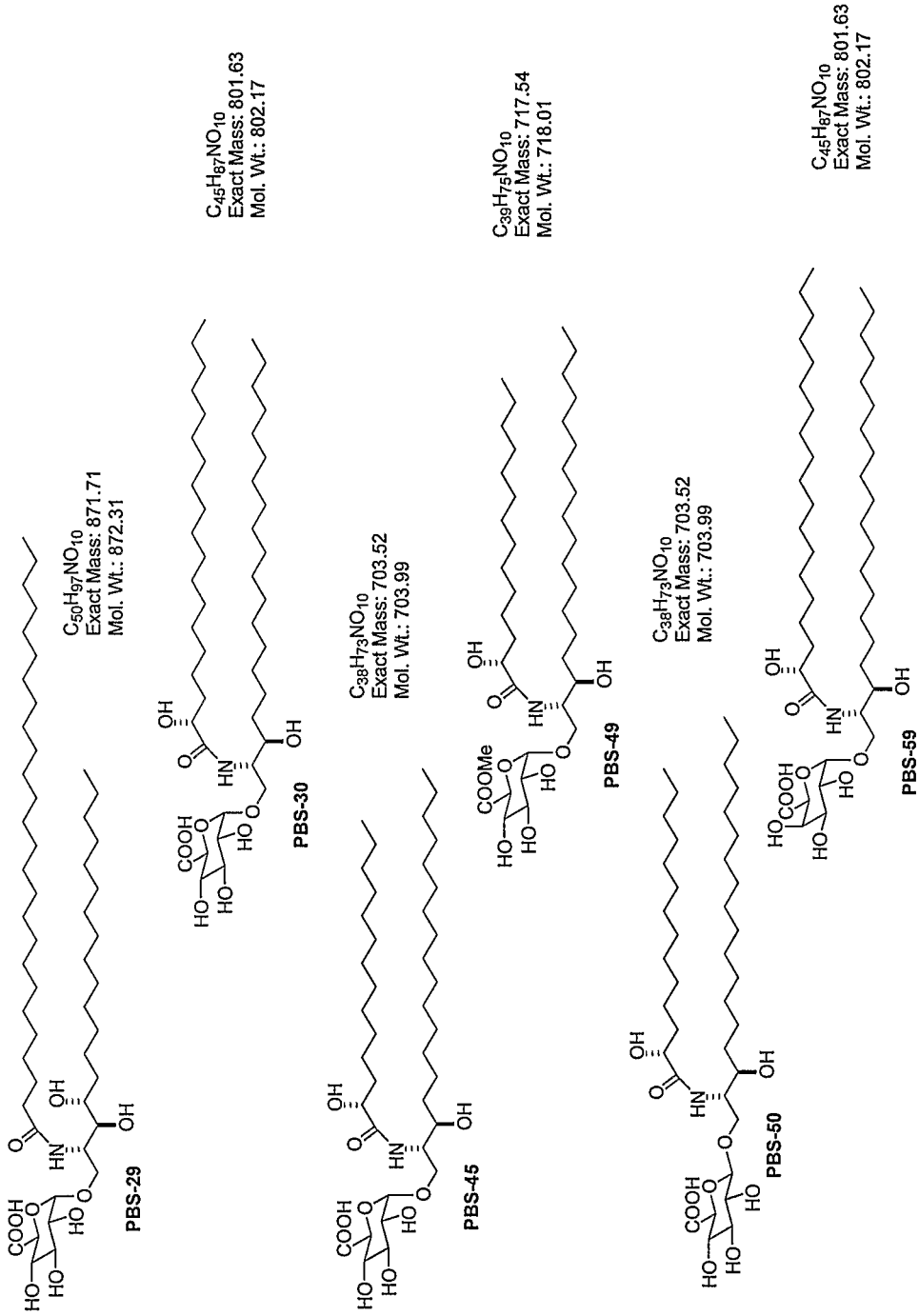
Figure 5:
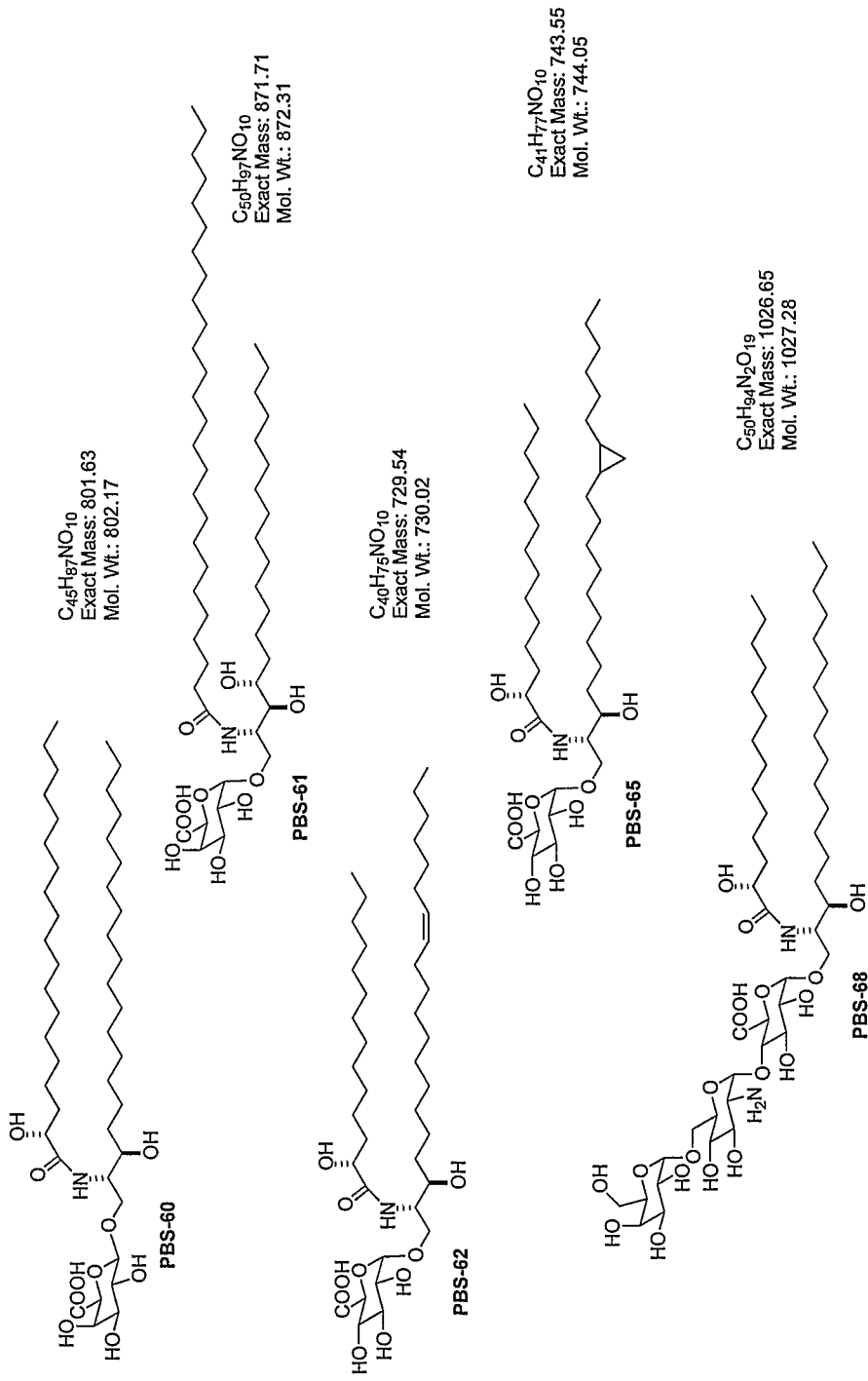

FIG. 5 depicts several synthetic glycolipids derived from bacteria of the class Alphaproteobacteria.

Figure 6:
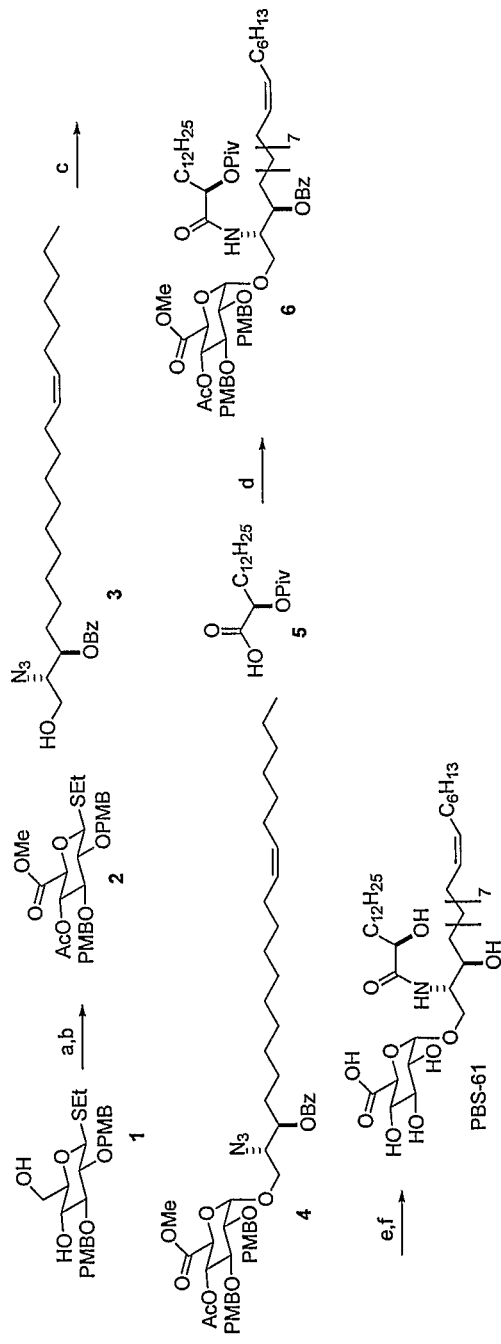

FIG. 6 depicts an exemplary synthetic scheme for glycolipid PBS 61.

DETAILED DESCRIPTION OF SEVERAL EMBODIMENTS

CD1-restricted T cells carry out both effector and helper functions and interact with a variety of cell types, including macrophages, dendritic cells, NK cells, T cells and B cells, thereby contributing to both innate and adaptive immune responses. A subset of these T cells, NKT cells, also known as CD1d-restricted T cells or CD1d tetramer+ T cells, are characterized by invariant TCRα chains, self lipid reactivity and rapid effector responses. These cells play an important role in a number of immune functions, including antimicrobial responses, antitumor immunity and in regulating the balance between tolerance and autoimmunity.

In the absence of foreign antigens, NKT cells are stimulated by exposure to $CD1^+$ antigen presenting cells, such as monocytes, dendritic cells (DC) and macrophages. Classes of self-antigens that can be presented to and recognized by NKT cells include phospholipids, such as phosphatidylinositol, phosphatidylethanolamine and phophatidylglycerol, as well as sphingolipids. However, not all classes elicit a response in NKT cells in terms of cytokine release.

NKT cells also are known to recognize α-galactosylceramide (αGal-Cer), a glycosphingolipid found in marine sponges. This molecule has no known immunological or other physiological function in mammals, but is widely used by investigators to study NKT activation. Prior to the present invention, activation of NKT by direct presentation of microbial glycolipids was not known.

NKT cells are rapidly activated upon stimulation by CD1d presented polar lipid antigens. "Activation," as the term is used herein and in the art, refers to secretion by NKT cells of IFN-γ, IL-4, IL-2, IL-10, IL-13, GM-CSF or TNF-α, or combinations of these cytokines, upon contact with CD1d presented stimulatory antigens. Alternatively, "activation" may refer to upregulated expression of cell-surface markers for activated T-cells, for example, CD69.

Activation of NKT cells in accordance with the invention comprises contacting an NKT cell, or more specifically, a T cell receptor (TCR) of the NKT cell, with a CD1d-complexed bacterial polar lipid. Glycolipids are suitable species of polar lipids. Thus, in some embodiments, activation of NKT cells comprises contacting an NKT cell with a bacterial glycolipid derived from a member of the Class Alphaproteobacteria. "A T cell receptor of an NKT cell," as the term is used herein, refers to the conserved, semi-invariant TCR of NKT cells comprising, e.g., Vα14-Jα18/Vβ8 in mice and Vα24-Jα18/Vβ11 in humans. "Contacting," as used herein, refers to the in vitro addition of bacterial glycolipid in solution to immobilized, soluble, or insoluble CD1d molecules, or to the in vivo administration of bacterial glycolipid to a subject having antigen presenting cells which express cell surface CD1d molecules.

Activation of NKT cells may be measured in vitro or ex vivo by any suitable method. An example of an in vitro test permitting evaluation of NKT cell activation is co-culturing NKT cells with antigen presenting cells (APC), such as dendritic cells (DC), in the presence of a bacterial glycolipid activator or putative activator, and subsequently assaying for IFN-γ or other secreted cytokines in the supernatant. Alternatively, activation of NKT cells can be measured ex vivo by administering a bacterial glycolipid antigen to a subject or by administering $CD1d^+$ antigen presenting cells after ex vivo contact with bacterial glycolipids to a subject. The NKT cells from these subjects can be isolated by, e.g., CD1d-tetramer staining and gating via flow cytometry, and subsequently assayed for surface CD69 (early T-cell activation antigen) and/or intracellular IFN-γ by suitable methods.

Alphaproteobacteria is a class in the phylum Proteobacteria comprised mostly of bacteria having two major phenotypes: purple non-sulfur bacteria and aerobic bacteriochlorophyll-containing bacteria. Bacterial members of the class of Alphaproteobacteria are primarily isolated from soil, lakes or ponds. Several members are known human pathogens.

The class Alphaproteobacteria includes six orders: Rhodospirillales, Rickettsiales, Rhodobacterales, Sphingomonadales, Caulobacterales and Rhizobiales (Garrity, G M et al., Taxonomic Outline of the Procaryotic Genera, BERGEY'S MANUAL of Systematic Bacteriology, $2^{nd}$ Ed, April 2001, incorporated herein by reference). Bacterial glycolipids which may be useful in activating NKT cells may be derived from members of any of these orders. However, members of orders Rickettsiales, Sphingomonadales and Rhizobiales are contemplated to be particularly suitable.

The order Rickettsiales includes three families: Rickettsiaceae, Ehrlichiaceae and Holosporaceae. Polar lipids derived from members of Ehrlichiaceae in the genus *Ehrlichia* are contemplated to be suitably used in methods of the invention. For example, *E. muris*-derived glycolipids may be suitable.

The order Sphingomonadales includes the family Sphingomonadaceae. Glycolipids derived from members of this family in the genus *Sphingomonas*, for example, from *S. capsulata*, are contemplated to be suitable.

The order Rhizobiales includes ten families: Rhizobiaceae, Bartonellaceae, Brucellaceae, Phyllobacteriaceae, Methylocystaceae, Beijerinckiaceae, Bradyrhizobiaceae, Hyphomicrobiaceae, Methylobacteriaceae and Rhodobiaceae. Glycolipids derived from members of Brucellaceae in the genus *Brucella* are contemplated to be suitably used in methods of the invention.

*Sphingomonas capsulata* is a pathogen of the Alphaproteobacteria class which is a gram-negative, lipopolysaccharide (LPS)-negative bacteria whose cell wall lipids have been extensively characterized. Glycolipids derived from the cell walls of these bacteria may be used to activate NKT cells in accordance with the invention.

Similarly, members of the genus *Ehrlichia* are gram-negative, LPS-negative bacteria whose cell wall lipids may be used to activate NKT cells. Although the cell membrane lipids of *Ehrlichia* are not as well-characterized as those of *Sphingomonas capsulata*, it is contemplated that members of this genus will function to activate NKT cells in suitable activation assays, as well as in vivo.

*Brucella* is another genus in this class known to be pathogenic. The four species of this genus that can infect humans include *B. abortus, B. suis, B. melitensis* and *B. canis*. Brucellosis disease in humans is characterized as either an acute febrile disease or a persistent disease with a wide variety of symptoms. It is a true zoonosis in that virtually all human infections are acquired from animals. Subclinical infection is common. In contrast to *Erlichia* and *Sphingomonas* spp., the outer cell membrane comprises a dominant LPS component and three main groups of proteins. It is contemplated that particular fractions or components of these bacterial cell membranes may be used to directly activate NKT cells in accordance with the invention.

As noted, bacterial glycolipids are suitably derived from bacteria of the class Alphaproteobacteria. "Derived from," refers to isolation and/or purification from bacterial sources, and also refers to de novo synthesis of bacterial compounds, or compounds rationally designed based on bacterial compounds, using suitable synthetic processes known in the art. As will be appreciated by one of ordinary skill in the art, "bacterial glycolipids" may also include heat killed or attenuated bacteria in the context of the methods of the invention. For example, contacting a NKT cell with a bacterial glycolipid suitably includes contacting a NKT cell with a heat killed or attenuated bacteria, as well as isolated or synthetic bacterial glycolipids.

The term "glycolipid" designates any compound containing one or more monosaccharide residues bound by a glycosidic linkage to a hydrophobic moiety such as an acylglycerol, a sphingoid, a ceramide (N-acylsphingoid) or a prenyl phosphate. In particular, one or more saccharides bound to a ceramide moiety may be particularly useful in activating NKT cells.

Bacterial glycolipids suitable for use in methods of activating NKT cells may be generally of the structural formula (I):

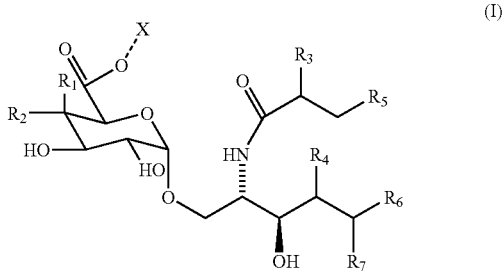

wherein - - - indicates either a single bond wherein X is H or lower alkyl, or an ionic bond wherein X is a counter ion; $R_1$ and $R_2$ are independently selected from the group consisting of —H, —OH, a monosaccharide and an oligosaccharide; $R_3$ is —H or —OH; $R_4$ is —H or —OH or, together with $R_7$, forms a double bond; $R_5$ and $R_6$ are independently C1-C30 alkyl, wherein the C1-C30 alkyl is saturated or unsaturated or comprises one or more cyclopropyl groups; and $R_7$ is —H or, together with $R_4$, forms a double bond. As used herein, the term "lower alkyl" is meant to refer to a straight or branched, saturated or unsaturated hydrocarbon radical having 1 to 4 carbon atoms. Specific examples of such hydrocarbon radicals are methyl, ethyl, propyl, isopropyl, butyl, isobutyl, t-butyl, ethenyl, propenyl, butenyl, isobutenyl, isopropenyl, formyl, acetyl, propionyl, butyryl or cyclopropyl. Also as used herein, a "counter ion" is any positively charged species that can associate via an ionic bond with a negatively charged carboxylate on the glycolipid.

Some representative examples of suitable bacterial glycolipids for complexing with CD1d molecules and activating NKT cells are depicted in FIG. 5. PBS 30, PBS 45 and PBS 59 were synthesized based on known *Sphingomonas* cell membrane molecules and were found to activate NKT cells in vitro. Conversely, PBS 50 and PBS 60 do not activate NKT cells. The remaining compounds depicted in FIG. 5 were rationally designed based on the following features determined to be common among glycolipids capable of activating NKT cells: 1) an alpha-type glycosidic linkage and 2) oxidation at the 6-position on the carbohydrate moiety of the glycolipid.

In some embodiments, activation of NKT cells by administration of a bacterial glycolipid in accordance with the invention may provide a means by which an immune response may be stimulated in a subject. An "immune response" as used herein refers to any elevated level of humoral or cellular response that is measurable in a subject in comparison to the subject's baseline, or unstimulated, state. Methods of measuring both humoral and cellular immune responses are well-known in the art. As will be appreciated, the in vivo response of NKT cells is influenced, in part, by the cellular environment during activation. $T_H1$ immune responses are characterized predominantly by release of, e.g., IL-2, IFN-γ, IL-12 and TNF-α. In contrast, $T_H2$ cytokines predominantly include IL-4, IL-5, IL-6, IL-10, and IL-13. The in vivo response of NKT cells may also be influenced by antigen concentration or prior, or repeated, antigen exposure. Activation may be further mediated by interactions with co-stimulatory molecules on NKT cells and APCs, e.g., CD40/CD40L interactions.

In addition to cytokine secretion, activated NKT cells are potently cytolytic via release of perforin and granzymes, as well as granulysin, and can contribute directly to bacterial cell and/or tumor cell killing via secretion of these molecules.

Thus, activating NKT cells in a subject by administration of an effective amount of a bacterial glycolipid to a subject may generate an anti-microbial immune response and thereby provide a means of treating an infection in the subject. The infection may be viral, bacterial or parasitic and the anti-microbial immune response may be sufficient to inhibit the growth of, or kill a microbe, including e.g., viruses, bacteria or parasites. Administration may be carried out by any method employed in the art, including intraperitoneal, intravenous, intramuscular, subcutaneous, transcutaneous, oral, nasopharyngeal or mucosal absorption, among others.

As mentioned, methods of the invention may also be employed in the treatment of cancer, or in promoting tumor rejection, by inducing an antihyperproliferative immune response in a mammal. "Treating" or "treatment" of cancer in a mammal includes one or more of: (1) inhibiting growth of the cancer, i.e., arresting its development, (2) preventing spread of the cancer, i.e. preventing metastases, (3) relieving the cancer, i.e., causing regression of the cancer, (4) preventing recurrence of the cancer, (5) palliating symptoms of the cancer, and (6) promoting rejection of one or more solid tumors.

In a particular embodiment, bacterial glycolipids in accordance with the invention can be administered as an adjuvant to improve vaccine efficacy when co-administered with a vaccine. As used herein the term "co-administration" or "co-administering" refers to administration of at least two components concurrently, i.e., simultaneously in time, or sequentially, i.e., administration of one component, followed by administration of the other component.

Adoptive transfer methods are based on administering cells that have been contacted with bacterial glycolipids ex vivo to stimulate an immune response in a subject. In some embodiments, the cells may be NKT cells that are activated ex vivo and injected into a subject to provide or enhance an immune response to, e.g., cancerous cells or microbes. In some embodiments, administration of activated NKT cells may induce an antihyperproliferative immune response to promote solid tumor rejection. In other embodiments, the cells may be antigen presenting cells that have been contacted with bacterial glycolipids ex vivo to allow complexing of the bacterial glycolipids with the CD1d molecules expressed by the antigen presenting cell, e.g., a dendritic cell. Antigen presenting cells can then be administered, e.g., by injection into the subject, to provide a suitable immune response. This method of administration allows for stimulation of the immune response with minimal exposure of the subject or the subject's cells to the bacterial glycolipids.

Activation of NKT cells may also be employed in methods of modulating autoimmunity or inhibiting allergen-induced hypersensitivity. Both direct administration of bacterial glycolipids, as well as adoptive transfer methods are contemplated for these particular treatments.

The following examples are provided to assist in a further understanding of the invention. The particular materials and conditions employed are intended to be further illustrative of the invention and are not limiting upon the reasonable scope thereof.

Example 1

In Vitro Stimulation of NKT Cells with Heat-Killed Bacteria

Bacterial strains *Sphingomonas capsulata* (ATCC 14666) and *Salmonella typhimurium* R71 were grown in Mueller-Hinton Agar. *Ehrlichia muris* were prepared as described by Ismail N et al., J. Immunol. 172, 1786-1800 (2004), incorporated herein by reference. Bacteria were heat killed by 2-hour exposure to 74° C. and $2.5-5\times10^6$ cfu equivalent/well were used for in vitro stimulation.

Stimulation assays were performed with whole spleen cells ($5\times10^5$ per 200 µl well) or with purified T cells and antigen presenting cells. T cell populations used in the assays comprised sorted CD1d-Gal-Cer+ mouse spleen cells ($5\times10^4$ per 200 µl well), human peripheral blood lymphocytes (PBL) ($5\times10^5$ per 200 µl well) (obtained after Ficoll centrifugation of heparinized blood) or human NKT cell lines ($2.5\times10^5$ per 200 µl well). Human Vα24 NKT cells were derived from PBL stimulated with αGal-Cer and were maintained by repeated rounds of stimulation with PHA and IL-2 in the presence of irradiated PBMC and EBV transformed B cells in vitro. Antigen presenting cells were dendritic cells that were derived from bone marrow, stimulated with GMCSF/IL-4 (2 ng/mL and 5 ng/mL, Biosource) and cultured at $2.5\times10^5$ per 200 µl well for mouse assays, and irradiated allogeneic human PBMC fresh or cultured for 5 days with recombinant human GMCSF/IL-4, (100 µg/mL of each cytokine, R&D Systems) ($2\times10^5$ per 200 µl well) for human assays. Cells were washed twice and starved for 6 hours in medium alone before addition to the stimulation experiments.

NKT cells were stimulated with heat-killed bacteria as indicated above for 48 hrs in 96 well round bottom plates in RPMI 1640 (Biofluids) supplemented with glutamine, antibiotics, $5\times10^{-5}$ M 2-ME and 10% FCS (mouse studies) or 5% AB serum (human studies). Concentrations of mouse and human IFN-γ. in the supernatant were measured at 48 hours using the respective ELISA kits (BD Bioscience, lower detection limit of 12.5 pg/ml).

Whole spleen cells were stimulated for 6 days with $5\times10^6$ heat killed bacteria or 100 ng/mL αGal-Cer, and the frequency of CD1d-αGal-Cer+ NKT cells were measured at stimulation and 2, 4 and 6 days post-stimulation.

At 6 days post stimulation, CD1d-αGal-Cer, CFSE and αB220 (BD Pharmingen) labeling and staining procedures were performed and cells were analyzed by FACS. To generate CD1d-αGal-Cer tetramers, a mixture of 5 µl of αGal-Cer (from 1 mg/ml stock solution in DMSO), 10 µl of PBS 0.5% Tween 20, 10 µl of biotinylated CD1d (1 mg/ml), and 75 µl of PBS was incubated at 37° C. for 1 hr, and lipid-loaded CD1d was purified by centrifugation dialysis and complexed with streptavidin-APC. (Benlagha K. et al., J. Exp. Med. 191, 1895-1903 (2000).) Cells were analyzed on a FACSCalibur (BD Biosciences) with CellQuest software.

Figure 1:
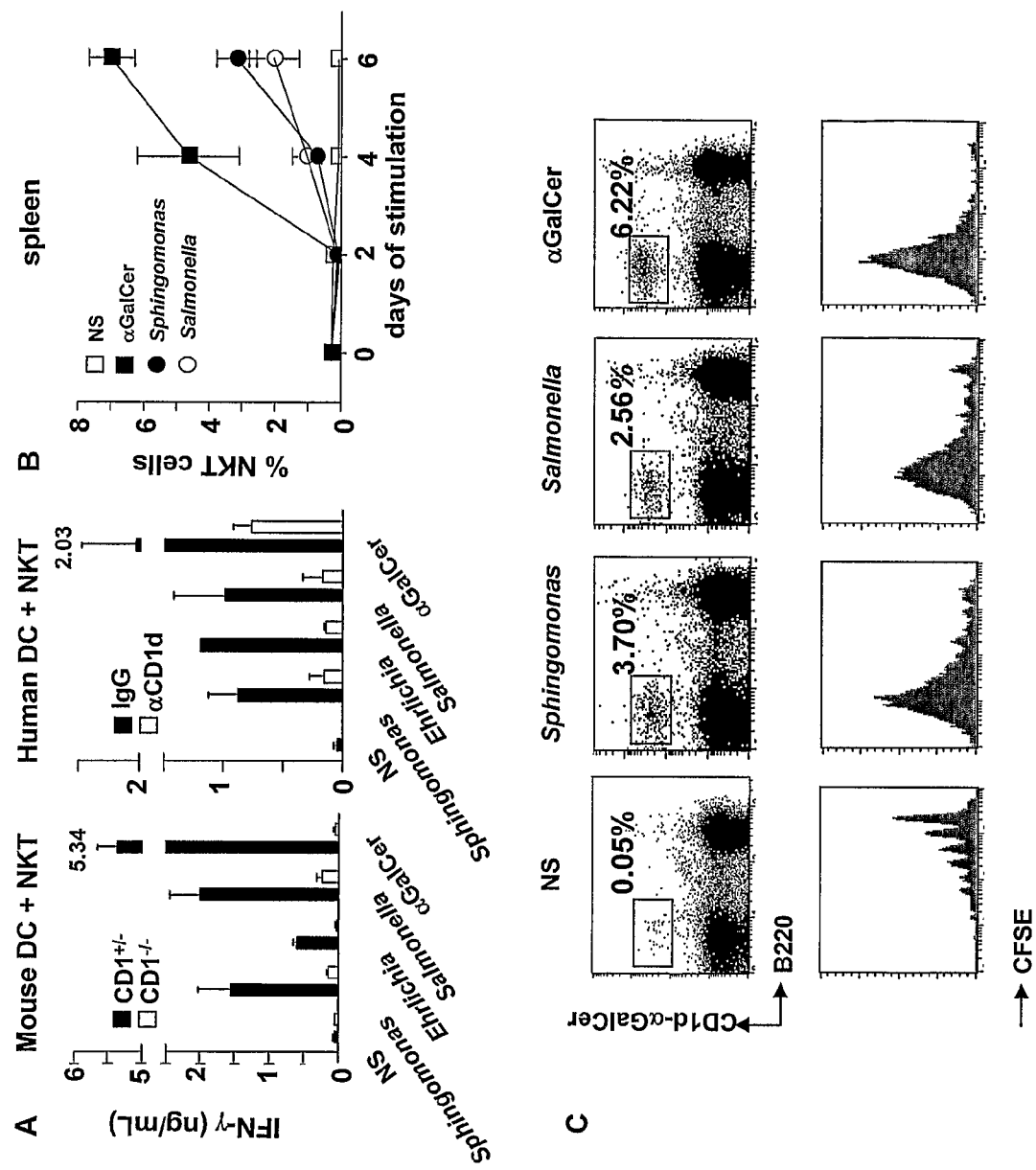
FIG. 1A depicts CD1d-dependent IFN-γ secretion by mouse and human NKT cells stimulated with heat-killed bacteria or αGal-Cer. Mean and standard deviation of 3 experiments.
FIG. 1B depicts NKT cell proliferation in a spleen cell culture stimulated with heat-killed bacteria or αGal-Cer. Data points show means and standard deviations from 3 separate experiments.
FIG. 1C depicts NKT cell proliferation in response to bacterial stimuli or αGal-Cer. Upper row, CD1d-αGal-Cer/B220 staining of spleen cells with NKT cell gate and percentage as indicated. Lower row, CFSE dilution profile of $5 \times 10^3$ gated NKT cells.

Results are reported in FIGS. 1A-C. Mouse CD1d tetramer-sorted NKT cells co-cultured with fresh bone marrow derived $CD1^{+/-}$ or $CD1^{-/-}$ DC secreted IFN-γ in a CD1d-dependent manner when stimulated with heat killed *Sphingomonas* and *Erlichia*, as well as control *Salmonella* and αGal-Cer. (FIG. 1A, left.) Similarly, human NKT cells co-cultured with PBMC-derived DC secreted IFN-γ in a CD1d-dependent manner upon stimulation, where CD1d dependence was illustrated using blocking with 1 µg/mL anti-CD1d antibodies or control IgG1. (FIG. 1A, right.) Whole spleen cell suspensions cultured in the presence of heat-killed bacteria for 6 days showed a marked expansion and proliferation of NKT cells, only slightly less than that induced by pure αGal-Cer. (FIG. 1B-C.)

Example 2

Differential Requirements for the IFN-γ Response to *Sphingomonas* and *Ehrlichia* Versus *Salmonella*

Whole spleen cells co-cultured with DC of genotype $MyD88^{-/-}$, $Trif^{lps2/lps2}$ and $MyD88^{-/-}Trif^{lps2/lps2}$ (lacking one or the two adaptors MyD88 and TRIF for TLR signaling) or $CD1^{-/-}$ were stimulated for 48 hours with $5\times10^6$ heat killed *Salmonella*, *Sphingomonas* or *Ehrlichia*. Concentrations of mouse and human IFN-γ. in the supernatant were measured at 48 hours using the respective ELISA kits (BD Bioscience, lower detection limit of 12.5 pg/ml).

DC were pulsed with heat-killed bacteria, prepared as described in Example 1 and added to human NKT cell preparations in the presence of IB4 (*Griffonia Simplicifolia* isolectin B4) (Vector Laboratories) which binds the terminal disaccharide of iGb3, but does not bind to αGal-Cer. IFN-γ production was measured at 48 hours.

$Hexb^{-/-}$ DC, which fail to generate iGb3 in the lysosome because they lack the b-hexosaminidase needed to remove the terminal GalNAc of iGb4, the precursor of iGb3, were pulsed with heat-killed bacteria as described above and added to NKT cell cultures. IFN-γ production was measured at 48 hours.

Figure 2:
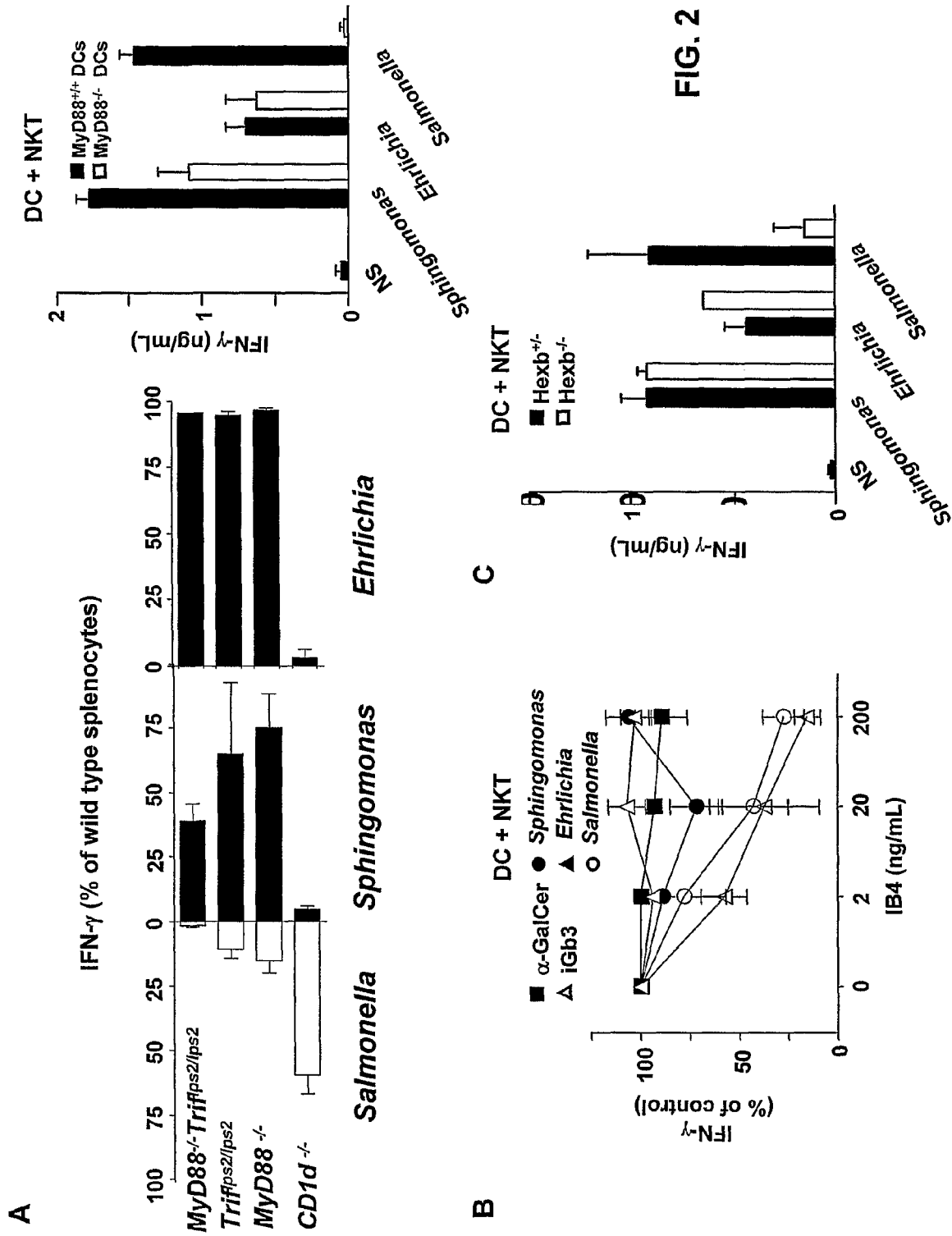
FIG. 2A depicts IFN-γ released by whole spleen cells cultured with heat killed *Salmonella typhimurium*, *Sphingomonas capsulata*, and *Ehrlichia muris* for 48 hours. Left panel, data shown as percentage of wild type control. Right panel, data shown as mean and standard deviation of two to three separate experiments.
FIG. 2B depicts the blockade of human NKT cell responses to DC plus antigen by lectin IB4. Similar data obtained in two experiments.
FIG. 2C depicts stimulation of mouse NKT cell responses to bacterial antigen presented by $Hexb^{+/-}$ or $Hexb^{-/-}$ DC. Similar data obtained in two experiments.

Results are reported in FIGS. 2A-C. In the whole spleen cell culture assay, *Salmonella*-induced IFN-γ was drastically reduced to 2-15% of control, on average, in the absence of either one or the two TLR adaptors (FIG. 2A). In sharp contrast, the splenic IFN-γ response to LPS-negative *Ehrlichia* and *Sphingomonas* was largely independent of MyD88 and TRIF. $CD1^{-/-}$ spleen cells lacking NKT cells failed to respond to *Sphingomonas* and *Ehrlichia*, whereas the response to *Salmonella* was only marginally reduced (FIG. 2A, left). Likewise, wild type NKT cells co-cultured with MyD88-deficient DC responded to *Sphingomonas* and *Ehrlichia* but not *Salmonella* (FIG. 2A, right). Altogether, these results suggested that in total spleens exposed to heat-killed *Salmonella*, IFN-γ production was initiated after TLR signaling of antigen presenting cells and subsequent recruitment of NKT cells as well as other cell-types such as NK cells. In contrast, IFN-γ stimulation by *Ehrlichia* and *Sphingomonas* was primarily dependent on NKT cells and CD1d with minimal contribution of TLR.

Similarly, lectin IB4 binding did not impair the stimulation of NKT cells by DC pulsed with heat-killed *Ehrlichia* or *Sphingomonas*, consistent with direct recognition of a distinct microbial antigen. However, the lectins readily blocked stimulation by *Salmonella* (FIG. 2B), suggesting that for the *Salmonella* NKT response, endogenous iGb3 is the likely ligand.

Hexb$^{-/-}$ DC pulsed with heat-killed *Ehrlichia* or *Sphingomonas* stimulated NKT cells as well as wild-type DC. (FIG. 2C) In contrast, *Salmonella*-pulsed Hexb$^{-/-}$ DC did not stimulate NKT cells.

Together, the results identify the endogenous ligand iGb3, rather than a microbial antigen, as the target of NKT cells in their response to *Salmonella* infection.

Example 3

NKT Cell Stimulatory Response to Synthetic Glycolipid Antigens

α-glucuronosylceramide (PBS 30) and α-galacturonosylceramide (PBS 59), derived from known Sphingomonadaceae cell membrane antigens, were synthesized as described in Example 5. PBS 50, a β-glucuronosylceramide, served as a control compound. The structures of these compounds are shown in FIG. 3A.

The immunological properties of the above compounds in NKT cells were measured. Human Vα24-Jα18 NKT cells and fresh purified mouse NKT cells were co-cultured with DC pulsed with αGal-Cer or synthetic glycolipid at concentrations ranging from 0.001 to 1000 ng/mL. IFN-γ production was measured at 48 hours as described above.

CD1d tetramers were prepared as described in Example 1 using synthetic glycolipids PBS 30, PBS 59 and PBS 50 and αGal-Cer, and were used to stain human NKT cells and mouse spleen cells.

Figure 3:
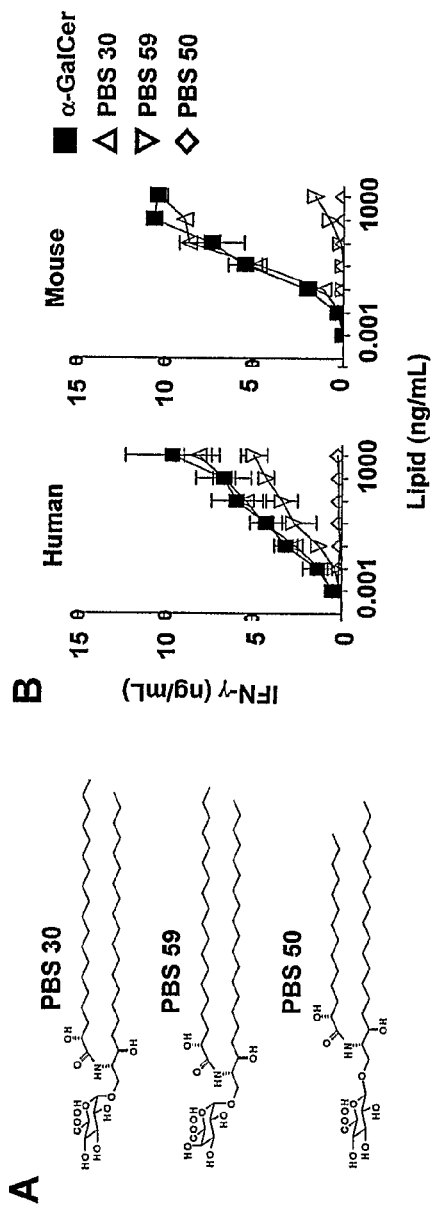
FIG. 3A depicts structures of synthetic *Sphingomonas* cell wall antigens. PBS 50 is a control β-glucuronosylceramide.
FIG. 3B depicts the IFN-γ response of a human Vα24-Jα18 NKT line and fresh purified mouse NKT cells stimulated by synthetic lipid antigens and DC. Data shown are the mean and standard deviation of two separate experiments.
FIG. 3C depicts CD1d tetramer staining of human NKT (upper row) and mouse spleen cells (lower row) with synthetic glycolipids. NKT cell gate and percentages are as indicated.
Figure 3:
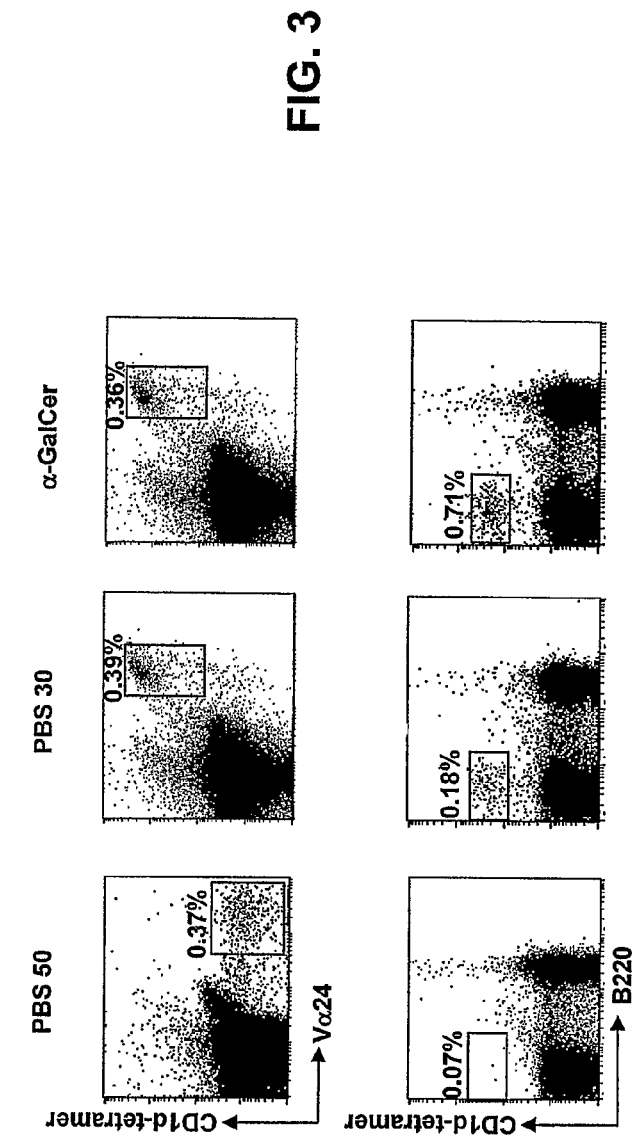

Results are shown in FIGS. 3 B-C. Both α-glucuronosylceramide (PBS 30) and to a lesser degree, α-galacturonosylceramide (PBS 59) strongly activated mouse and human NKT cell proliferation as well as IFN-γ secretion, whereas control β-glucuronosylceramide (PBS 50) did not (FIG. 3B). Tetramers of CD1d-α-glucuronosylceramide (PBS 30) stained all human NKT cells and ~25% of mouse NKT cells (FIG. 3C). Thus, these findings revealed that the lipids replacing LPS in the cell wall of some species of Gram-negative bacteria may be directly recognized by the conserved TCR of innate-like NKT cells.

Example 4

In Vivo Role of NKT Cells During Microbial Infection

CD1d$^{-/-}$ mice were generated at the University of Chicago, Jα18$^{-/-}$ mice were obtained from Dr. Taniguchi, Chiba University (Japan) and Hexb$^{-/-}$ mice were obtained from R. Proia, National Institutes of Health. All mice were in the C57/BL6 background. In all cases, littermates obtained from heterozygous matings were genotyped by PCR and used for comparative analysis. All mice were raised in a pathogen-free environment at University of Chicago according to the Institutional Animal Care and Use Committee guidelines.

Six- to seven-week old C57/BL6 mice were intravenously inoculated with 100 μl *Sphingomonas* (1×10$^7$), *Ehrlichia* (1×10$^8$) or *Salmonella* (1×10$^6$) suspended in PBS. Twenty-four hours post-infection, isolated NKT cells gated as tetramer$^+$/B220$^-$ were analyzed by FACS for surface CD69 (early T-cell activation antigen) and intracellular IFN-γ. Results, shown in FIG. 4A, confirm that NKT cells are activated and secrete IFN-γ within 24 hours after infection in vivo.

To determine whether hexb is required for antigen processing in response to *Salmonella* and *Sphingomonas* infection in vivo, Hexb$^{+/-}$ and Hexb$^{+/-}$ littermates were challenged intraperitoneally with 5×10$^6$ *Sphingomonas* or *Salmonella*. Two hours post-challenge, 5×10$^6$ CFSE-labelled Vα14 transgenic thymocytes were intrasplenically injected in a volume of 50 μl (Bendelac A. et al., J. Exp. Med. 184, 1285-12293 (1996), incorporated herein by reference). At 24 hours post-challenge, intracellular staining for IFN-γ was performed. Results are shown in FIG. 4B. The difference between Hexb$^{+/-}$ and Hexb$^{+/-}$ was statistically significant only for *Salmonella* challenged mice, demonstrating that IFN-γ production by NKT cells in response to *Salmonella* infection requires lysosomal iGb3, whereas the response of NKT cells to *Sphingomonas* does not require lysosomal iGb3.

To characterize the role of NKT cells in controlling infection in vivo, Jα18$^{-/-}$ and CD1$^{-/-}$ mice and their littermate controls were injected intravenously with either 5×10$^6$ or 1×10$^6$ *Sphingomonas*. Bacterial burden in the lungs was assessed at intervals indicated in FIG. 4C. Bacterial counts were performed after tissue homogenization in 0.5% Triton X-100 and cultured for colony formation. The results demonstrate that both Jα18$^{-/-}$ and CD1$^{-/-}$ mice had delayed bacterial clearance compared to heterozygous littermate controls, with up to 12-14 times higher bacterial load in the lung at early time points.

For survival experiments, Jα18$^{-/-}$ and CD1$^{-/-}$ mice and their littermate controls were injected intravenously with a high dose of 5×10$^8$ *Sphingomonas*. Dead or moribund (euthanized) mice were recorded every 2-4 hours post-infection. The results, shown in FIG. 4D, demonstrate that infection with a high dose of *Sphingomonas* was rapidly lethal in wild-type mice, whereas a majority of NKT deficient mice survived.

To test whether lethality was associated with cytokine release, *Sphingomonas* (1×10$^7$) was intravenously injected in Jα18$^{-/-}$ and CD1$^{-/-}$ mice and their littermate controls. At intervals specified in FIG. 4E, serum levels of IFN-γ and IL-12 p40 were measured. The results indicate that the lethal outcome in wild-type mice was associated with the explosive release of IFN-γ and IL-12 in the serum, whereas NKT deficient mice produced significantly less cytokines.

For *Ehrlichia* infection experiments, mice were infected intraperitoneally with 500 μl of a 10$^{-1}$ dilution of *Ehrlichia muris* stock. The *Ehrlichia* load in the lungs, livers and spleens of CD1d$^{-/-}$ and control littermates was determined by real-time PCR of the *Ehrlichia* dsb gene (Ismail, N. et al., J. Immunol. 172, 1786-1800 (2004)) at 2 and 7 days post-infection. Results, reported in FIG. 4F, show that NKT deficient mice demonstrate an inability to clear *Ehrlichia*.

Example 5

Synthesis of Bacterial Glycolipid PBS 61

FIG. 6 depicts a suitable route of synthesis for PBS 61. To a vigorously stirred solution of compound "1" (Ando, H.; Manabe, S.; Nakahara, Y.; Ito, Y. Angew. Chem. Int. Ed. 2001, 40, 4725-4728.) (453 mg, 0.976 mmol) in $CH_2Cl_2$ (3 mL) and water (1.5 mL) was added TEMPO (60.8 mg, 0.390 mmol) and bis(acetoxy)iodobenzene (BAIB) (345 mg, 1.07 mmol) to produce intermediate compound "2" in FIG. 6. Additional BAIB (345 mg, 1.07 mmol) was added after 1 hour. The reaction was stirred until TLC indicated complete conversion of the starting material (~1.5 hour). The reaction mixture was extracted with $CH_2Cl_2$ twice and the combined organic layers were dried over $MgSO_4$ and concentrated. A short flash column ($SiO_2$, $CH_3OH/CH_2Cl_2$ 1:10) afforded crude glucuronic acid. A solution of crude glucuronic acid in $CH_2Cl_2$ (3 mL) was treated with a freshly prepared ethereal solution of diazomethane until the evolution of gas ceased. The reaction mixture was then treated with AcOH (2 mL) and concentrated in vacuo. Flash column chromatography ($SiO_2$, EtOAc/hexanes 1:4-1:3) afforded corresponding methyl glucuronate (186 mg, 0.378 mmol, yield 39% of two steps). $^1H$ NMR ($CDCl_3$) δ7.31-7.27 (m, 4H), 6.87-6.86 (m, 4H), 4.83-4.67 (m, 4H), 4.49 (d, J=9.8 Hz, 1H), 3.87-3.80 (m, 2H), 3.78 (s, 3H), 3.51 (t, J=7.8 Hz, 1H), 3.39 (t, J=8.8 Hz, 1H), 2.80-2.70 (m, 2H), 1.32 (t, J=7.3 Hz, 3H). $^{13}C$ NMR ($CDCl_3$) δ169.65, 159.47, 159.40, 130.65, 130.10, 129.71, 114.02, 113.89, 86.01, 84.83, 80.36, 75.28, 75.26, 71.91, 55.34, 52.79, 25.29, 15.13. High resolution fast atom bombardment mass spectrometry (thioglycerol+Na+matrix) m/e ([M+Na]+) 515.1716 (100.0%); calculated 515.1714. The methyl glucuronate (186 mg, 0.378 mmol) was dissolved in $CH_2Cl_2$ (10 mL) and $Et_3N$ (0.5 mL) followed by the introduction of a catalytic amount of DMAP (20 mg) and $Ac_2O$ (0.2 mL). The solvent was removed in vacuo after 12 hours and the residue was chromatographed ($SiO_2$, EtOAc/hexane 1:4) to afford the product (172 mg, 0.329 mmol, 87% yield) as clear oil. $^1H$ NMR ($CDCl_3$) δ7.31-7.18 (m, 4H), 6.88-6.85 (m, 4H), 5.12 (t, J=9.8 Hz, 1H), 4.83-4.61 (m, 4H), 4.47 (d, J=9.8 Hz, 1H), 3.86 (d, J=10.3 Hz, 1H), 3.80 (s, 3H), 3.71 (s, 3H), 3.65 (t, J=8.8 Hz, 1H), 3.49 (t, J=8.8 Hz, 1H), 2.82-2.68 (m, 2H), 1.95 (s, 3H), 1.32 (t, J=7.3 Hz, 3H). $^{13}C$ NMR ($CDCl_3$) δ169.72, 167.94, 159.63, 159.48, 130.38, 130.29, 130.02, 129.66, 113.99, 85.56, 82.80, 80.61, 76.64, 75.49, 75.22, 71.33, 55.47, 52.92, 25.17, 20.89, 15.15. High resolution fast atom bombardment mass spectrometry (thioglycerol+Na+matrix) m/e ([M+Na]+) 557.1827 (100.0%); calculated 557.1822.

To prepare intermediate compound "6," a mixture of compound "2" (172 mg, 0.329 mmol), compound "3" (150 mg, 0.328 mmol), and 2,6-di-tert-butyl-4-methylpyridine (67.6 mg, 0.329 mmol) in toluene (3 mL) was stirred with 4 Å molecular sieves (300 mg) for 1 h at room temperature. Next, dimethyl(methylthio)sulfonium triflate (66.8 mg, 0.329 mmol) was added, and stirring was continued for 8 hours. The mixture was concentrated and passed through a $SiO_2$ plug using 1:1 EtOAc/hexanes. The solvent was removed in vacuo and the residue was chromatographed ($SiO_2$, EtOAc/hexane 1:5-1:4) to afford the product "4" (61.1 mg, 0.0657 mmol, mixture of α-β-anomers, 20% yield). A solution of compound "4" (61.1 mg, 0.0657 mmol, mixture of α-β-anomers) in pyridine (10 mL) and water (2 mL) was treated with a stream of hydrogen sulfide for 15 minutes. The solution was stirred for 12 hours, and then hydrogen sulfide was bubbled again for 15 minutes. The reaction mixture was stirred for another 12 hours. The solvent was evaporated under vacuum and the residue was co-evaporated with toluene. The residue was dissolved in $CH_2Cl_2$ (10 mL) followed by the introduction of 5 (43.1 mg, 0.131 mmol). A solution of dicyclohexylcarbodiimide (DCC) (27.0 mg, 0.131 mmol) and dimethylaminopyridine (DMAP) (6.3 mg, 0.052 mmol) in $CH_2Cl_2$ was added, and stirring was continued for 6 hours. The mixture was concentrated and passed through a $SiO_2$ plug using 1:1 EtOAc/hexanes. The solvent was removed in vacuo and the residue was chromatographed ($SiO_2$, EtOAc/hexane 1:5-1:4) to afford the product "6" (22.3 mg, 0.0184 mmol, 28% yield of α-anomer). $^1H$ NMR ($CDCl_3$) δ8.07-8.04 (m, 2H), 7.61-7.58 (m, 1H), 7.47-7.44 (m, 2H), 7.27-7.16 (m, 4H), 6.87-6.81 (m, 4H), 6.67 (d, J=7.8 Hz, 1H), 5.36-5.29 (m, 3H), 5.18 (t, J=5.9 Hz, 1H), 5.00 (t, J=9.3 Hz, 1H), 4.79 (d, J=3.4 Hz, 1H), 4.74-4.54 (m, 4H), 4.52-4.49 (m, 1H), 4.14 (d, J=9.8 Hz, 1H), 3.85-3.74 (m, 8H), 3.69-3.62 (m, 4H), 3.55 (dd, J=9.3, 3.4 Hz, 1H), 2.01-1.96 (m, 7H), 1.88-1.78 (m, 2H), 1.36-1.09 (m, 55H), 0.90-0.87 (m, 6H). $^{13}C$ NMR ($CDCl_3$) δ177.19, 170.04, 169.84, 168.71, 166.45, 159.60, 159.40, 133.53, 130.76, 130.01, 129.46, 128.73, 114.03, 113.94, 98.56, 78.49, 78.19, 74.49, 73.97, 73.18, 71.18, 69.18, 67.96, 55.48, 52.92, 50.91, 49.38, 38.99, 34.16, 32.14, 31.99, 29.99, 29.86, 29.80, 29.65, 29.57, 29.19, 27.42, 27.30, 25.81, 25.57, 25.15, 24.84, 22.90, 20.91, 14.34. High resolution fast atom bombardment mass spectrometry (thioglycerol+Na+matrix) m/e ([M+Na]+) 1236.7557 (100.0%); calculated 1236.7539.

Preparation of PBS-61: Compound "6" (22.3 mg, 0.0184 mmol) was dissolved in tetrahydrofuran (THF) (1 mL) and water (0.5 mL) followed by the introduction of trifluoroacetic acid (TFA) (2 mL). The reaction was stirred until TLC indicated complete conversion of the starting material to a lower spot (~1.0 h). The reaction mixture was diluted by toluene and then concentrated in vacuo. The dialcohol was obtained as a clear glass (10.0 mg, 0.0103 mmol, yield 56%) after column chromatography ($SiO_2$, MeOH/$CH_2Cl_2$ 1:40-1:24) $^1H$ NMR ($CDCl_3$) δ8.02-8.00 (m, 2H), 7.64-7.61 (m, 1H), 7.50-7.46 (m, 2H), 6.67 (d, J=7.8 Hz, 1H), 5.35-5.33 (m, 2H), 5.22-5.18 (m, 1H), 5.08 (t, J=6.4 Hz, 1H), 4.98 (t, J=9.8 Hz, 1H), 4.82 (d, J=3.9 Hz, 1H), 4.51-4.50 (m, 1H), 4.22 (d, J=9.8 Hz, 1H), 3.99 (dd, J=10.2, 3.4 Hz, 1H), 3.93 (t, J=9.8 Hz, 1H), 3.72 (s, 3H), 3.58 (dd, J=9.3, 3.4 Hz, 1H), 3.40 (dd, J=10.3, 7.4 Hz, 1H), 2.11 (s, 3H), 2.05-1.98 (m, 4H), 1.88-1.78 (m, 2H), 1.36-1.09 (m, 64H), 0.89-0.86 (m, 6H). $^{13}C$ NMR ($CDCl_3$) δ177.99, 170.94, 170.44, 168.67, 167.14, 134.07, 130.15, 130.01, 129.19, 128.92, 99.47, 74.98, 74.60, 72.23, 71.76, 71.51, 69.23, 68.35, 53.06, 51.61, 39.11, 32.28, 32.13, 31.99, 31.78, 29.86, 29.73, 29.63, 29.57, 29.40, 29.19, 27.42, 27.22, 25.68, 25.07, 22.91, 22.87, 20.97, 14.35. High resolution fast atom bombardment mass spectrometry (thioglycerol+Na+matrix) m/e ([M+Na]+) 996.6404 (100.0%); calculated 996.6388. The dialcohol (10.0 mg, 0.0103 mmol) was dissolved in MeOH (1 mL) and THF (1 mL) followed by addition of NaOMe (0.2 mL of 1 M NaOMe solution in MeOH) and 3 drops of water. The mixture was stirred for 12 hours and then water (2 mL) was added. The reaction mixture was concentrated in vacuo and the residue was chromatographed ($SiO_2$, $CHCl_3$/MeOH/$H_2O$ 60:30:4) to afford PBS-61 (5.0 mg, 0.069 mmol, 67% yield). $^1H$ NMR (DMSO-d6 0.7 ml with 1 drop of DCl and 3 drops of $D_2O$, 55° C.) δ5.36-5.34 (m, 2H), 4.79 (d, J=3.4 Hz, 1H), 3.94 (t, J=5.9 Hz, 1H), 3.88 (d, J=9.7 Hz, 1H), 3.82-3.79 (m, 1H), 3.71-3.63 (m, 2H), 3.58-3.56 (m, 1H), 3.50 (t, J=9.3, 1H), 3.38 (t, J=9.3 Hz, 1H), 3.30 (dd, J=9.3, 3.4 Hz, 1H), 2.01-1.99 (m, 4H), 1.60-1.55 (m, 2H), 1.36-1.09 (m, 64H), 0.90-0.87 (m, 6H). $^{13}C$ NMR (DMSO-d6 0.7 ml with 1 drop of DCl and 3 drops of $D_2O$, 55° C.) δ174.21, 171.39, 130.29, 100.46, 100.38, 73.35, 72.37, 71.54, 69.98, 68.02, 53.22, 41.09, 34.93, 34.22, 31.92, 31.75, 31.56, 29.93, 29.71, 29.32, 28.89, 27.26, 25.70, 24.97, 22.68, 14.54. High resolution fast atom bombardment mass spectrometry (thioglycerol+Na+matrix) m/e ([M+Na]+) 752.5289 (100.0%); calculated 752.5284.

All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

We claim:

1. A method of activating a natural killer T (NKT) cell comprising contacting the NKT cell with a pharmaceutical composition comprising an isolated synthetic compound of formula (I):

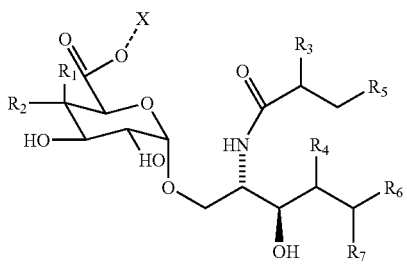

wherein:
- - - indicates a single bond wherein X is methyl or H or an ionic bond wherein X is a counter ion;
$R_1$ is H and $R_2$ is —OH;
$R_3$ is —H or —OH;
$R_4$ is —OH, H, or, together with $R_7$, forms a double bond;
$R_5$ and $R_6$ are independently C1-C30 alkyl, wherein the C1-C30 alkyl is saturated or unsaturated or comprises one or more cyclopropyl groups; and
$R_7$ is —H or, together with $R_4$, forms a double bond.

2. The method of claim 1, wherein:
X is methyl;
$R_1$ is —H;
$R_2$ is —OH;
$R_3$ is —OH;
$R_4$ is —OH;
$R_5$ is C11 alkyl;
$R_6$ is C13 alkyl; and
$R_7$ is —H.

3. The method of claim 1, wherein the compound of formula (I) is complexed with a CD1d molecule.

4. The method of claim 3, wherein the CD1d molecule is expressed by a cell.

5. The method of claim 4, wherein the cell is an antigen presenting cell.

6. The method of claim 5, wherein the antigen presenting cell is a dendritic cell.

7. The method of claim 3, wherein the CD1d molecule comprises a tetramer.

8. The method of claim 1, wherein the compound of formula (I) is selected from the following compounds:
PBS-49, wherein X is methyl; $R_1$ is —H; $R_2$ is —OH; $R_3$ is —OH; $R_4$ is —H; $R_5$ is $C_{11}$ alkyl; $R_6$ is $C_{13}$ alkyl; and $R_7$ is —H;
PBS-45, wherein X is H; $R_1$ is —H; $R_2$ is —OH; $R_3$ is —OH; $R_4$ is —H; $R_5$ is $C_{11}$ alkyl; $R_6$ is $C_{13}$ alkyl; and $R_7$ is —H;
PBS-29, wherein X is H; $R_1$ is —H; $R_2$ is —OH; $R_3$ is —H; $R_4$ is —OH; $R_5$ is $C_{23}$ alkyl; $R_6$ is $C_{13}$ alkyl; and $R_7$ is —H;
PBS-30, wherein X is H; $R_1$ is —H; $R_2$ is —OH; $R_3$ is —OH; $R_4$ is —H; $R_5$ is $C_{16}$ alkyl; $R_6$ is $C_{15}$ alkyl; and $R_7$ is —H;
PBS-62, wherein X is H; $R_1$ is —H; $R_2$ is —OH; $R_3$ is —OH; $R_4$ is —H; $R_5$ is $C_{11}$ alkyl; $R_6$ is $C_{15}$ alkyl comprising one double bond; and $R_7$ is —H; and
PBS-65, wherein X is H; $R_1$ is —H; $R_2$ is —OH; $R_3$ is —OH; $R_4$ is —H; $R_5$ is $C_{11}$ alkyl; $R_6$ is $C_{16}$ alkyl comprising one cyclopropyl group; and $R_7$ is —H.

9. The method of claim 1, wherein the pharmaceutical composition does not include any naturally sourced compound of formula (I).

10. A method of activating a natural killer T (NKT) cell comprising contacting the NKT cell with a pharmaceutical composition comprising a synthetic compound of formula (I):

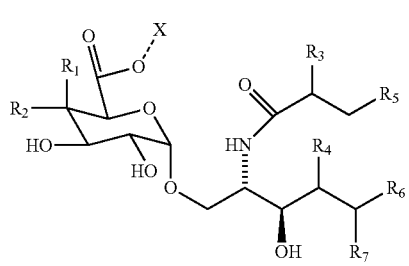

wherein formula (I) is selected from the following compounds:
PBS-49, wherein X is methyl; $R_1$ is —H; $R_2$ is —OH; $R_3$ is —OH; $R_4$ is —H; $R_5$ is $C_{11}$ alkyl; $R_6$ is $C_{13}$ alkyl; and $R_7$ is —H;
PBS-45, wherein X is H; $R_1$ is —H; $R_2$ is —OH; $R_3$ is —OH; $R_4$ is —H; $R_5$ is $C_{11}$ alkyl; $R_6$ is $C_{13}$ alkyl; and $R_7$ is —H;
PBS-29, wherein X is H; $R_1$ is —H; $R_2$ is —OH; $R_3$ is —H; $R_4$ is —OH; $R_5$ is $C_{23}$ alkyl; $R_6$ is $C_{13}$ alkyl; and $R_7$ is —H;
PBS-30, wherein X is H; $R_1$ is —H; $R_2$ is —OH; $R_3$ is —OH; $R_4$ is —H; $R_5$ is $C_{16}$ alkyl; $R_6$ is $C_{15}$ alkyl; and $R_7$ is —H;
PBS-62, wherein X is H; $R_1$ is —H; $R_2$ is —OH; $R_3$ is —OH; $R_4$ is —H; $R_5$ is $C_{11}$ alkyl; $R_6$ is $C_{15}$ alkyl comprising one double bond; and $R_7$ is —H; and
PBS-65, wherein X is H; $R_1$ is —H; $R_2$ is —OH; $R_3$ is —OH; $R_4$ is —H; $R_5$ is $C_{11}$ alkyl; $R_6$ is $C_{16}$ alkyl comprising one cyclopropyl group; and $R_7$ is —H.

* * * * *